United States Patent [19]

Pesa et al.

[11] 4,301,077

[45] Nov. 17, 1981

[54] PROCESS FOR THE MANUFACTURE OF 1-4-BUTANEDIOL AND TETRAHYDROFURAN

[75] Inventors: Frederick A. Pesa, Aurora; Anne M. Graham, Northfield, both of Ohio

[73] Assignee: Standard Oil Company, Cleveland, Ohio

[21] Appl. No.: 218,856

[22] Filed: Dec. 22, 1980

[51] Int. Cl.$^3$ .................. C07C 27/04; C07C 29/136; C07D 307/08
[52] U.S. Cl. .............................. 260/346.11; 568/858; 568/864
[58] Field of Search .................. 260/346.11; 568/858, 568/864

[56] References Cited

U.S. PATENT DOCUMENTS 3,853,922  12/1974  Yamaguchi et al. ........... 260/346.11

*Primary Examiner*—Richard Raymond
*Attorney, Agent, or Firm*—Gary R. Plotecher; Herbert D. Knudsen; Larry W. Evans

[57] ABSTRACT

Oxygenated $C_4$ hydrocarbons, such as maleic anhydride, are hydrogenated to tetrahydrofuran and/or 1,4-butanediol by a process comprising contacting the hydrocarbon with hydrogen at hydrogenation conditions in the presence of less than 25 wt. % water, based on the weight of the hydrocarbon, and a ruthenium-containing hydrogenation catalyst, such as the catalyst of the formula $$Ru\ Ni\ Co\ Zn_{0.4}.$$

10 Claims, No Drawings

PROCESS FOR THE MANUFACTURE OF 1-4-BUTANEDIOL AND TETRAHYDROFURAN

BACKGROUND OF THE INVENTION

1. Field of the Invention

This invention relates to the manufacture of tetrahydrofuran and 1,4-butanediol. In one aspect, the invention relates to the catalytic hydrogenation of oxygenated $C_4$ hydrocarbons, such as maleic anhydride, while in another aspect, the invention relates to the use of ruthenium-containing hydrogenation catalysts.

2. Description of the Prior Art

The art is replete with processes for manufacturing tetrahydrofuran and 1,4-butanediol from oxygenated $C_4$ hydrocarbons. A recent example is U.S. Pat. No. 4,155,919 which teaches a single-stage process for converting maleic anhydride into 1,4-butanediol and/or tetrahydrofuran by contacting the maleic anhydride with hydrogen at specified conditions in the presence of a catalyst containing nickel, molybdenum and/or tungsten, and optionally zirconium and/or niobium. Reaction conditions include a temperature from 170°–215° C. and a pressure of from 125–200 bars. Other known processes are cited in that teaching over columns 1–4. Still other processes are known and include U.S. Pat. Nos. 3,113,138, 3,957,827 and 3,370,067. While all of these processes are useful for their intended purpose, all are subject to improvement. Two disadvantages common to many of these processes are the need to use high pressures, e.g. in excess of 1500 psi, and generally unsatisfactory product yield.

SUMMARY OF THE INVENTION

According to the process of this invention, tetrahydrofuran and 1,4-butanediol are manufactured from an oxygenated $C_4$ hydrocarbon selected from the group consisting of maleic anhydride, maleic acid, succinic anhydride, succinic acid, γ-butyrolactone and mixtures of two or more of these, by contacting the oxygenated $C_4$ hydrocarbon with hydrogen at a temperature of about 175° C. to about 275° C. and a pressure of about 750 psi to about 1500 psi in the presence of less than about 25 wt. % water, based on the weight of the hydrocarbon, and a catalyst of the formula

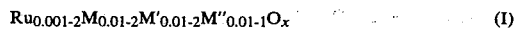

where
M is at least one of nickel and palladium,
M' is at least one of iron, cobalt, rhodium, osmium, iridium and platinum,
M" is at least one of zinc and cadmium, and
x is a number sufficient to satisfy the valency requirements of the other elements present.

This process is particularly useful for converting in a single step maleic anhydride and/or γ-butyrolactone at a relatively low pressure to a good product yield of at least one of tetrahydrofuran and 1,4-butanediol.

DETAILED DESCRIPTION OF THE INVENTION

Reactants

The oxygenated $C_4$ hydrocarbons here used as the starting material are maleic anhydride, maleic acid, succinic anhydride, succinic acid, γ-butyrolactone and various mixtures comprising two or more of these materials. Maleic anhydride and γ-butyrolactone are preferred starting materials and a mixture of the two is particularly preferred. γ-Butyrolactone is an excellent solvent for maleic anhydride and a mixture of from about 1 to about 20 wt. %, based upon the total weight of the mixture, of maleic anhydride in γ-butyrolactone is a typical method of employing maleic anhydride as a starting material.

Hydrogen is generally employed as an undiluted gas but it can be diluted with another gas if desired. If a diluent gas is used, it is typically an inert gas, i.e. nonreactant with the process starting materials, catalyst and products at process conditions.

Catalysts

The catalysts here used are ruthenium-containing catalysts of the formula

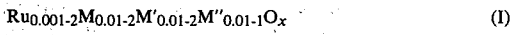

where M, M', M" and x are as previously defined. Preferably, M is nickel, M' is iron, cobalt or rhodium and M" is zinc. Preferably, the molar ratio of ruthenium is between about 0.01 and 1.5, of M and M' between about 0.1 and 1.5, and of M" between 0.05 and 0.8. More preferably, the molar ratio of ruthenium is between about 0.1 and 1.5, of M and M' between about 0.5 and 1.5, and of M" between about 0.1 and 0.8. A preferred catalyst of this invention is of the formula

The mixed metal oxide catalyst of this invention can be prepared in any one of a number of different methods. A typical and convenient method begins with dissolving in water a salt, e.g. a hydrated chloride, of each metal component of the catalyst and then adjusting the pH of the solution to above 7, typically above 8. The resulting slurry is then heated, filtered and washed thoroughly, dried, calcined and subsequently ground. The resulting catalytic composition can be used either in the 100% active form or in a diluted form, i.e. supported or unsupported. Suitable support materials include silica, titania, alumina, zirconia, silicon carbide, boron, various phosphates, etc. with low surface area (about 2 m²/g) alumina a preferred support material. The support material can be incorporated into the catalyst along with the catalytic components or the catalytic composition can be coated and/or impregnated onto or into a support core. If a support is used, the catalytic composition is generally present in an amount of at least about 1 wt. %, based on the combined weight an amount of at least about 5 wt. %. Preferably, the catalysts used in this invention are supported.

Process Conditions

The process of this invention can be conducted in either the liquid or gas phase or in a mixed liquid-gas phase. The reaction temperature is typically between about 175° and about 275° C. and preferably between about 200° and about 250° C. The reaction pressure is typically between about 750 and about 1600 psi and preferably between about 1000 and 1500 psi. These pressures are typically lower than those employed in the prior art processes.

Stoichometric amounts of oxygenated $C_4$ hydrocarbon and hydrogen are required for this process, but since hydrogen is both generally used in an undiluted form and is the principal source of pressure of the process, hydrogen is generally present in a large molar access. The amount of catalyst required to practice this invention can vary widely and is dependent upon a number of different factors, such as the starting hydrocarbon, hydrogen pressure, contact time, reactor size and design, etc. Typically, sufficient catalyst is packed into a fixed- or fluid-bed reactor and the reactants passed over and/or through a catalyst bed for continuous operation. In a batch operation, typically between about 0.1 and about 10 wt. %., and preferably between about 1 and about 5 wt. %, of active (without support) catalyst is used based upon the weight of the oxygenated $C_4$ hydrocarbon to be converted.

As indicated in the preceding paragraph, the process of this invention can be practiced in virtually any kind of reactor that can accommodate the reaction conditions and accordingly, the contact time between the process reagents and catalyst will vary. In a continuous operation, such as a fixed- or fluid-bed reactor, typical contact times range from about 30 sec to about 5 min although they can be shorter or longer as desired. In a batch operation, the time will vary with the reaction starting materials, catalyst and conditions but a time between about 2 and 14 hours is usual.

The presence of water in the reaction mass is not desirable because water is believed to inhibit the hydrogenation of the oxygenated $C_4$ hydrocarbons to tetrahydrofuran and 1,4-butanediol. Consequently, the addition of water to the reaction mass is generally avoided. Water that is present in the hydrocarbon feed or water that is generated in situ is typically not detrimental, at least to a significant degree, on the overall efficiency of this process. However, where very wet hydrocarbon feeds are to be used or significant water is generated in situ, there water is preferably vented from the system. Generally, the process of this invention is practiced in the presence of less than about 25 wt. % water, based on the weight of the hydrocarbon or hydrocarbon mixture, and preferably in the presence of less than about 10 wt. % water.

This invention can be practiced either neat or in the presence of a solvent. Any solvent that will not prevent the hydrogenation of the process hydrocarbons can be used but solvents that are not extraneous to the process are preferred. For example, dioxane and $C_1$-$C_4$ alkanols are suitable solvents but because they must be eventually removed from the reaction product, they are less desirable than γ-butyrolactone or tetrahydrofuran. Obviously, if 65 -butyrolactone is the starting oxygenated $C_4$ hydrocarbon, then the process is conducted neat. However, where one of the other oxygenated $C_4$ hydrocarbons or some mixture of these hydrocarbons is the starting material, then γ-butyrolactone can be used as a solvent. The use of γ-butyrolactone in such a manner is well known and is more fully discussed in U.S. Pat. No. 4,155,919. Sufficient solvent is employed to dissolve the starting oxygenated $C_4$ hydrocarbons and, as indicated before, when maleic anhydride is the starting material, it is generally dissolved in about 80-99 wt. %, based on the weight of the resulting mixture, of γ-butyrolactone.

Products

Tetrahydrofuran and 1,4-butanediol are the products produced by this invention. These products are generally produced in tandem, i.e. together, and the relative amounts in which they are produced is dependent upon a number of factors. One such factor is the degree of catalyst exposure to hydrogen. Those catalysts that have had only limited exposure favor the production of 1,4-butanediol while catalysts that have had extensive exposure favor the production of tetrahydrofuran. In short, the more the catalyst is exposed to hydrogen, the more the production of tetrahydrofuran is favored.

Other factors influencing product distribution are temperature and molar concentrations of zinc and/or cadmium in the catalyst. Generally, lower temperatures (less than 245° C.) and higher (greater than 0.27) molar levels of zinc favor the production of tetrahydrofuran.

This invention also produces small quantities of by-products, the most common being n-propanol and n-butanol. These products are usually a result of the degradation of 1,4-butanediol and thus their amounts can be restrained by promptly removing the diol from the reaction product.

Both tetrahydrofuran and 1,4-butanediol are commercial commodities and have a plurality of uses. For example, 1,4-butanediol is used in the production of polybutylene terephthalate and RIM urethanes while tetrahydrofuran is a useful solvent for high polymers, such as polyvinyl chloride and as a comonomer polyether polyols.

The following examples are illustrative embodiments of this invention. Unless otherwise noted, all parts and percentages are by moles.

SPECIFIC EMBODIMENTS

Catalyst Preparation

The catalysts used in these experiments were mixed metal oxides coated on Alundum ®. They were prepared by dissolving a salt, typically the hydrated chloride, of each metal (0.015 mole) in a total of 250 ml of water and stirred for 30 minutes. Sodium hydroxide (50% by weight in water) was added dropwise until the pH reached and maintained 8.3 (approximately 10 ml). The resulting slurry was heated near boiling for 30 minutes with constant stirring and then cooled. The pH was rechecked and adjusted, if necessary to at least 7.5. The mixture was then filtered and washed thoroughly, reslurried, and filtered and washed again. The solid mixed oxide was dried overnight at 125° C., calcined 3 hours at 353° C. and subsequently ground to pass a 140 mesh (U.S. Standard) screen.

Norton SA-5223 Alundum ®, a fused-alumina (50 g, 10/30 mesh) was placed into a round pint glass jar. Distilled water (2.5 g) was sprayed onto the Alundum ® and the jar was rolled for 10 minutes on a ball miller. Water (2.5 g) was again sprayed onto the Alundum ® followed by an additional 10 minutes of rolling. The mixed metal oxide (2.8 g) prepared above and commercial zinc oxide (0.28 g) were added in two equal portions with 15 minutes of rolling after each. The coated catalyst was dried overnight at 125° C. and then calcined for 3 hours at 350° C. The coated catalyst thus prepared contained approximately 5 wt % active material and a ratio of zinc atoms to atoms of the other metals of approximately 0.4:1. These catalysts had surface areas of about 2 m$^2$/g and pore volumes between about 0.06 and about 0.09 cc/g.

Apparatus and Procedure

A high-pressure flow system was used in these experiments and included a 40 cc fixed-bed reactor. The reactor was packed with 40 cc of catalyst and the system charged to the desired pressure with hydrogen. Hydrogen was allowed to pass over the catalyst bed at 50 cc/min while the temperature was increased, first to 150° F., and then in 50° F. steps at 20 minute intervals until the desired experimental temperature was reached. The hydrogen flow was then increased to 150 cc/min and the system was left to catalyst conditioning for 2 to 20 hours, the exact time varying with the individual experiments. In some cases, the temperature was increased to 275° C. instead of the experimental temperature and the catalyst exposed to 150 cc/min of hydrogen for 1 hour and then 652 cc/min for an additional hour. Once the catalyst was conditioned to the desired degree, the experiment began by adjusting the hydrogen feed rate to the desired value and by introducing the oxygenated $C_4$ hydrocarbon, usually maleic anhydride in $\gamma$-butyrolactone, at an appropriate rate. Product was then collected for approximately 2 hours in a cooled pre-run condenser and discarded. The product to be analyzed was then collected in a second condenser during the third hour. Off-gas was sampled and analyzed at the start and finish of this third hour. The temperature was continuously monitored using a thermocouple 1½ in. from the top of the catalyst bed.

At the completion of each run, the product stream was switched back to the pre-run condenser for shutdown. The second condenser holding the product for analysis was then warmed, emptied, product weighed and analyzed. Liquid products were analyzed by gas chromotography using a Perkin-Elmer 3920B connected to a computer for programmed integration.

Results and Discussion

EXAMPLE 1

A catalyst of the formula RuNiCoZn (III) (5% active supported on Norton SA-5223 Alundum ®) was used. The catalyst was heated to 220° C. from room temperature by increasing the temperature 50° F. every 20 min under a hydrogen flow of 50 cc/min. The catalyst was then heated an additional two hours under a hydrogen flow of 150 cc/min at the experimental conditions, i.e. 220° C. and 1000 psi. $\gamma$-Butyrolactone, neat, was then introduced to the reactor at 13.3 cc/hr and the hydrogen flow increased to 652 cc/min. Analysis of the liquid product showed that 47.6% of the $\gamma$-butyrolactone was converted to 1,4-butanediol with a selectivity of 83.4%. Selectivity to the combination of n-propanol and n-butanol was less than 2%.

EXAMPLE 2 and 3

Example 1 was repeated except a catalyst with the formula Ru Ni Co $Zn_{0.4}$ (II) (again 5% active supported on Norton SA-5223 Alundum ®) was used instead of catalyst III and the hydrocarbon feed was maleic anhydride (MAH) dissolved in $\gamma$-butyrolactone ($\gamma$-BL). The results are reported in Table I.

TABLE I

| Ex | wt % MAH | % Conver $\gamma$-Bl | Diol (% Sel) | THF (% Sel) |
|---|---|---|---|---|
| 2 | 10 | 17.4 | 51.8 | 11.3 |
| 3 | 20 | −10.7 | 20.67 | 25.0 |

In both examples 2 and 3, 100% of the maleic anhydride was hydrogenated. In example 3, the -10.7 indicates that there was a net increase in the moles of $\gamma$-butyrolactone. The data shows that as the percent of maleic anhydride increases, the selectivity of the reaction for 1,4-butanediol (Diol) decreases while the selectivity for tetrahydrofuran (THF) increases. The reduction in the percent conversion of the $\gamma$-butyrolactone that accompanies the increase in maleic anhydride concentration is believed the result of the larger amount of water present from the hydrogenation of maleic anhydride and this inhibited the hydrogenation of the $\gamma$-butyrolactone.

EXAMPLES 4-8

The conditions of Example 1 were again repeated except in some examples water was added to the hydrocarbon feed. The results are reported in Table II.

TABLE II

| Ex | % $H_2O$ Added[1] | wt % MAH | % Conv $\gamma$-Bl | Diol (% Sel) | THF (% Sel) |
|---|---|---|---|---|---|
| 4 | 0 | 0 | 26.3 | 96.2 | 0.8 |
| 5 | 2 | 0 | 20.4 | 87.5 | 0 |
| 6 | 10 | 0 | 22.4 | 67.6 | 0.6 |
| 7 | 0 | 10 | 10.9 | 8.5 | 88.8 |
| 8 | 20 | 10 | 6.9 | 26.9 | 30.3 |

[1]Based on the total weight of oxygenated hydrocarbon feed

In examples 7 and 8, 100% of the maleic anhydride was hydrogenated. Also in exmaples 7 and 8, the catalyst was conditioned by exposing it to hydrogen for 1 hour at 150 cc/min followed by a second exposure to hydrogen at 652 cc/min, both hours at 275° C. and 1000 psi.

As the data shows, increased levels of water inhibit the conversion of $\gamma$-butyrolactone and decrease the selectivity to both 1,4-butanediol and tetrahydrofuran. The large selectivity to tetrahydrofuran reported in Example 7 is believed the result of the use of a catalyst having had extensive exposure to hydrogen.

CONTROL A AND EXAMPLES 9-14

The conditions of Example 1 were again repeated except 10% maleic anhydride in $\gamma$-butyrolactone was used as the feed in all cases. The catalysts of Examples 13 and 14 were conditioned under the same conditions as the catalysts of Examples 7 and 8. The results are reported Table III.

TABLE III

| Ex/Cont | Catalyst | Temp (°C.) | % Conv $\gamma$-Bl | Diol (% Sel) | THF (% Sel) |
|---|---|---|---|---|---|
| A | Ru Co Ni | 245 | 13.2 | 5.3 | 49.8 |
| 9 | Ru Co Ni $Zn_{0.4}$ | 245 | 22.5 | 86.7 | 3.7 |
| 10 | Ru Co Ni $Zn_{0.4}$ | 245 | 26.0 | 77.3 | 6.7 |
| 11 | Ru Co Ni $Zn_{0.4}$ | 245 | 24.5 | 74.7 | 3.2 |
| 12 | Ru Co Ni $Zn_{0.8}$ | 245 | 66.7 | 14.1 | 55.7 |
| 13 | Ru Co Ni $Zn_{0.4}$ | 220 | 10.9 | 8.5 | 88.8 |
| 14 | Ru Co Ni $Zn_{0.8}$ | 220 | 13.1 | 4.8 | 68.3 |

In all cases, conversion of the maleic anhydride was complete. The tetrahydrofuran selectivity reported in Example 14 is relatively low. The weight of the product collected in this experiment was substantially less than theoretical and it is believed that some of the produced tetrahydrofuran was evaporated and swept from the reactor with the off-gases.

The data in Table III demonstrates that increased levels of zinc have a dramatic effect on the rate and activity of the reaction and the selectivity for tetrahydrofuran production. As the data shows, increased levels of zinc shows in increased selectivity for tetrahydrofuran.

EXAMPLES 15-18

A catalyst having the same composition as the catalyst of Examples 2 and 3 was here used as well as the conditions of Example 1 except as indicated in Table IV. The oxygenated hydrocarbon feed in all cases was 10 wt % maleic anhydride in γ-butyrolactone and in all cases the maleic anhydride was completely hydrogenated.

TABLE IV

| Ex | Temp (°C.) | Press (psi) | % Conv γ-B1 | Diol (% Sel) | THF (% Sel) |
|---|---|---|---|---|---|
| 15 | 245 | 1000 | 22.5 | 86.7 | 3.7 |
| 16 | 245 | 1300 | 47.5 | 80.6 | 3.1 |
| 17 | 220 | 1000 | −1.0 | 0 | 11.5 |
| 18 | 240 | 1000 | 27.1 | 81.8 | 6.8 |

The negative conversion of γ-butyrolactone reported in Example 17 reflects a net increase in the number of moles of γ-butyrolactone. The catalyst in each example was conditioned at process temperature and pressure for two hours in the presence of 150 cc/min of hydrogen.

The data of Table IV shows that an increase in pressure increases the conversion of γ-butyrolactone but decreases the selectivity for both 1,4-butanediol and tetrahydrofuran. An increase in the conversion of γ-butyrolactone is also observed as the temperature is increased yet the selectivity here for 1,4-butanediol also increases.

Although the invention has been described in considerable detail through the preceding examples, these examples are for the purpose of illustration only. Variations and modifications can be made by one skilled in the art without departing from the spirit and scope of the invention.

We claim:

1. A process for the manufacture of at least one of tetrahydrofuran and 1,4-butanediol from an oxygenated C4 hydrocarbon selected from the group consisting of maleic anhydride, maleic acid, succinic anhydride, succinic acid, γ-butyrolactone and mixtures comprising at least two of these, the process comprising contacting the oxygenated C4 hydrocarbon with hydrogen at a temperature of about 175° C. to about 275° C. and a pressure of about 750 psi to about 1500 psi in the presence of less than about 25 wt % water, based on the weight of the oxygenated hydrocarbon, and a catalyst of the formula $$Ru_{0.01-2}M_{0.01-2}M'_{0.01-2}M''_{0.01-1}O_x$$

where

M is at least one of nickel and palladium,

M' is at least one of iron, cobalt, rhodium, osmium, iridium and platinum,

M" is at least one of zinc and cadmium, and x is a number sufficient to satisfy the valency requirements of the other elements present.

2. The process of claim 1 where the molar ratio of ruthenium is between about 0.01 and 1.5, of M and M' between about 0.1 and 1.5, and of M" between about 0.05 and 0.8.

3. The process of claim 2 where M' is iron, cobalt, or rhodium.

4. The process of claim 3 where M" is zinc.

5. The process of claim 4 where M is nickel.

6. The process of claim 5 where M' is cobalt.

7. The process of claim 6 where the oxygenated C4 hydrocarbon is maleic anhydride, γ-butyrolactone, or a mixture of maleic anhydride and γ-butyrolactone.

8. The process of claim 7 where the oxygenated C4 is a mixture of about 1 to about 20 wt %, based on the total weight of the mixture, of maleic anhydride dissolved in γ-butyrolactone.

9. A process for the manufacture of 1,4-butanediol from maleic anhydride, the process comprising contacting a mixture of about 1 to about 20 wt %, based on the total weight of the mixture, of maleic anhydride dissolved in γ-butyrolactone with hydrogen at a temperature of about 230° C. to about 250° C. and a pressure of about 1000 psi to about 1300 psi in the presence of less than about 10 wt % water, based on the total weight of the oxygenated hydrocarbon mixture, and a catalyst of the formula $$Ru_{0.01-2}M_{0.1-2}M'_{0.1-2}Zn_{0.3-0.5}O_x \qquad (IV)$$

where

M is at least one of nickel and palladium,

M' is at least one of iron, cobalt and rhodium, and x is a number sufficient to satisfy the valency requirements of the other elements present.

10. A process for the manufacture of tetrahydrofuran from γ-butyrolactone, the process comprising contacting γ-butyrolactone with hydrogen at a temperature of about 175° C. to about 230° C. and a pressure of about 750 psi to about 1300 psi in the presence of less than about 10 wt. % water, based on the total weight of γ-butyrolactone, and a catalyst of the formula $$Ru_{0.01-2}M_{0.1-2}M'_{0.1-2}Zn_{0.4-1}O_x \qquad (V)$$

where

M is at least one of nickel and palladium,

M' is at least one of iron, cobalt and rhodium, and x is a number sufficient to satisfy the valency requirements of the other elements present.

* * * * *